(12) United States Patent
Amplatz

(10) Patent No.: US 6,638,257 B2
(45) Date of Patent: Oct. 28, 2003

(54) INTRAVASCULAR FLOW RESTRICTOR

(75) Inventor: Kurt Amplatz, St. Paul, MN (US)

(73) Assignee: AGA Medical Corporation, Golden Valley, MN (US)

( * ) Notice: Subject to any disclaimer, the term of this patent is extended or adjusted under 35 U.S.C. 154(b) by 0 days.

(21) Appl. No.: 10/087,570

(22) Filed: Mar. 1, 2002

(65) Prior Publication Data

US 2003/0167068 A1 Sep. 4, 2003

(51) Int. Cl.[7] .................................................. A61M 5/24
(52) U.S. Cl. ........................................................ 604/200
(58) Field of Search ............................... 606/200, 110, 606/113, 114, 127; 623/1.12, 1.18, 1.49, 1.51, 1.5, 1.52

(56) References Cited

U.S. PATENT DOCUMENTS

| | | | | |
|---|---|---|---|---|
| 4,619,246 A | * | 10/1986 | Molgaard-Nielsen et al. | 128/899 |
| 4,793,348 A | * | 12/1988 | Palmaz | 606/194 |
| 5,064,435 A | * | 11/1991 | Porter | 623/23.7 |
| 5,522,822 A | * | 6/1996 | Phelps et al. | 606/151 |
| 5,683,411 A | * | 11/1997 | Kavteladze et al. | 606/200 |
| 5,725,552 A | * | 3/1998 | Kotula et al. | 606/213 |
| 5,846,261 A | * | 12/1998 | Kotula et al. | 606/213 |
| 6,123,715 A | | 9/2000 | Amplatz | |
| 6,368,338 B1 | * | 4/2002 | Konya et al. | 606/200 |
| 6,375,670 B1 | * | 4/2002 | Greenhalgh | 606/200 |
| 6,511,496 B1 | * | 1/2003 | Huter et al. | 606/200 |

* cited by examiner

Primary Examiner—Michael J. Milano
Assistant Examiner—Nguyen Victor
(74) Attorney, Agent, or Firm—Thomas J. Nikolai; Nikolai & Mersereau, P.A.

(57) ABSTRACT

An intravascular flow restrictor comprises a braided tubular structure designed to be placed in the main pulmonary artery for limiting blood pressure in the lungs. The braided structure is designed to be collapsed for placement in a delivery catheter but when ejected from the delivery catheter, assumes a substantially larger diameter disk shaped device having one or more longitudinal channels or passways therethrough.

18 Claims, 3 Drawing Sheets

INTRAVASCULAR FLOW RESTRICTOR

BACKGROUND OF THE INVENTION

I. Field of the Invention

The present invention relates generally to intravascular devices for treating certain medical conditions, and, more particularly, relates to an intravascular flow restrictor for reducing blood pressure down stream of the location where the flow restrictor is placed.

II. Description of the Prior Art

In the normal heart, the right side pumps blood to the lungs, which is a relatively easy task, while the left side of the heart has the more difficult job of pumping blood all around the body. As a result, the pressure in the left ventricle (pumping chamber) is generally about five times that in the right ventricle, and the wall of the left ventricle is thicker than that of the right. There are a number of heart defects in which there is excessive blood flow to the lungs. Many defects that involve holes in the septum allow blood to flow from the high pressure left side of the heart to the lower pressure right side. This results in an increase in the pressure on the right and causes too much blood to be pumped to the lungs. The body's natural reaction to this is to constrict or narrow the blood vessels in the lungs in an effort to limit this excess blood flow. Over a period of time, this narrowing of the pulmonary arteries causes a thickening of the pulmonary arteries due to the increased workload, which leads ultimately to closure of smaller lung arteries which further reduces the blood flow into the lungs.

There is less and less left to right shunting of blood into the pulmonary arteries, and eventually the resistance is such that the shunt is reversed, i.e., right to left shunting occurs. This process is called pulmonary vascular disease and ultimately results in low oxygen levels and cyanosis and increased hemoglobin levels in the blood of the patient. It is the damage caused by prolonged pulmonary hypertension that generally prohibits late repair of cardiac defects. As children with Down's syndrome have a propensity to develop pulmonary vascular disease due to the fact that they tend to have larger holes in the heart, fewer small lung arteries and smaller airways, surgical repair is generally carried out fairly early in life, although timing will vary depending on the exact heart defect.

For example, in the case of ventricular septal defects (VSD), especially where there are multiple openings, it may not be possible to surgically close the defects. In the case of neonates, they may not be strong enough to survive an open-heart procedure required to repair multiple "Swiss cheese" septal defects. If an infant with VSD develops symptoms of congestive heart failure in the first few months of life, less traumatic palliative surgery may be attempted. Palliative surgery reduces the damage of the defect without correcting the underlying cause. One such palliative treatment is pulmonary artery (PA) banding. In the case of VSD, PA banding increases the resistance to blood flow through the pulmonary artery, preventing excessive shunting of blood from the left ventricle through the defects to the right ventricle.

In the case of an infant or young child with abnormally elevated pressure in the pulmonary artery, surgery is often considered too dangerous, but pulmonary banding may be effective. This procedure requires the surgeon to place a restrictive band around the pulmonary artery, thus reducing the blood flow into the lungs, and preventing the need for the body to form its own restriction. If successful, the normal development of pulmonary hypertension may be slowed or stopped, and surgical repair of the hole may be possible at a later date.

PA banding surgery, while less traumatic than open-heart surgery, still requires a thoracotomy to expose the pulmonary artery so that a constrictive band can be sutured around the pulmonary artery. The PA band reduces the diameter of the pulmonary artery and thereby restricts the amount of blood pumped into the lungs. Such an operation may reduce the blood flow from one-half to one-third of its previous volume. Pulmonary artery blood pressure distal to the band is reduced as a result of the volume restriction usually to about 50%–70% of the pulmonary artery pressure prior to banding.

While pulmonary artery banding is less risky than open heart surgery, it still carries the usual risks of surgery, such as bleeding, infection, pulmonary embolism, heart failure, etc. The special risk of the pulmonary artery banding procedure is making the band too tight or too loose. If it is too tight, too little blood will flow to the lungs and patient may become blue. If it is too loose, it will not eliminate the congestion of the lungs and will not protect the lungs from injury and pulmonary vascular disease.

Thus, a need exists for a non-surgical procedure, which is less traumatic than current procedures involving pulmonary artery banding, for restricting blood flow to the lungs in patients having congenital cardiac conditions which may cause pulmonary vascular disease such as, for example, left sided hypo plastic syndrome where flow restrictions are placed into the individual pulmonary arteries. The present invention meets that need without the risk of surgery, producing pain or large scar of the chest.

SUMMARY OF THE INVENTION

In accordance with the present invention, there is provided a device that is adapted to be placed and anchored within the vascular system using a transvascular approach for restricting or limiting blood flow to the lungs, liver or other organs. It comprises a collapsible medical device made from a plurality of metal strands that are braded into a woven metal fabric having a proximal end and a distal end, each end having a clamping member for securing each end of the woven metal fabric to thereby gather the strands and inhibit unraveling of the strands. The woven metal fabric has an expanded, preset configuration shaped to create a restriction in a blood vessel, the expanded preset configuration being generally in a shape of a round disk of a predetermined thickness dimension and outer diameter and having at least one lumen extending through the thickness dimension of the disk. The disk, formed from the woven metal fabric, is deformable to a lesser cross-sectional dimension for delivery by way of a guide catheter routed through a channel in a patient's body. The woven metal fabric has a memory property causing the device to return to its expanded, preset disk configuration when unconstrained.

The device is adapted to be deformed into its lesser cross-sectional dimension for placement in a catheter where the catheter may then be advanced through the vascular system until its distal end is disposed at a desired release site, such as beyond the ostium of the main pulmonary artery or into the individual right and left pulmonary arteries when treating pulmonary vascular disease. The device is then made to exit the distal end of the delivery catheter and when unconstrained, will lodge within the pulmonary artery and limit the volume of blood delivered from the right ventricle through the lumen of the device. The flow restrictor of the present invention finds other applications in treating a variety of medical conditions as is hereinafter described and claimed.

In accordance with a further feature of the invention, the hollow interior of the disk-shaped device may include a fibrous material insert for enhancing the occlusion of blood flow through the device except by way of the device's lumen(s).

DESCRIPTION OF THE DRAWINGS

Other features and advantages of the invention will become apparent to those skilled in the art from the following detailed description of a preferred embodiment, especially when considered in conjunction with the accompanying drawings in which.

DETAILED DESCRIPTION OF THE PREFERRED EMBODIMENT

The present invention provides a percutaneous catheter directed treatment of patients having malformed vascular system structures, such as shunt paths between the left and right side of the heart, transposition of the great arteries (TGA), transhepatic portosystemic shunts and protein-losing enteropathy following a Fontan operation.

Figure 1:
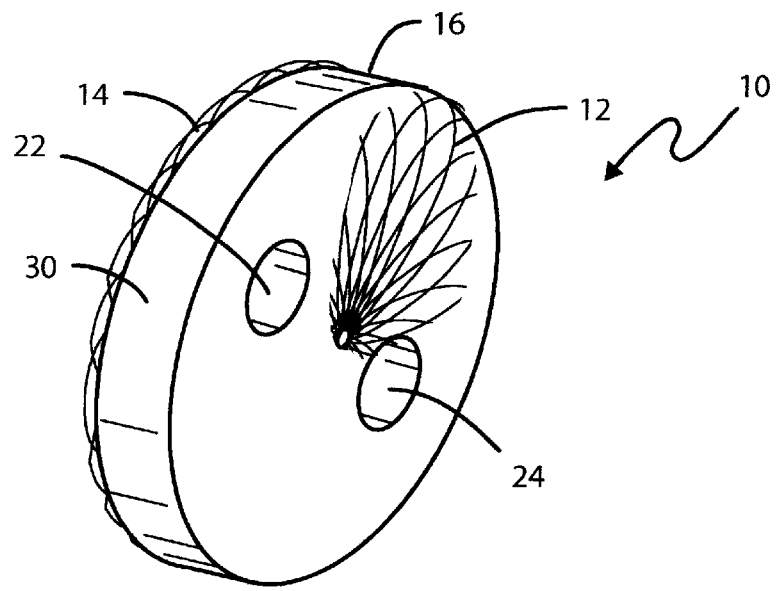
FIG. 1 is a perspective view of a collapsible medical device for use as a flow restrictor in its expanded state.
Figure 2:
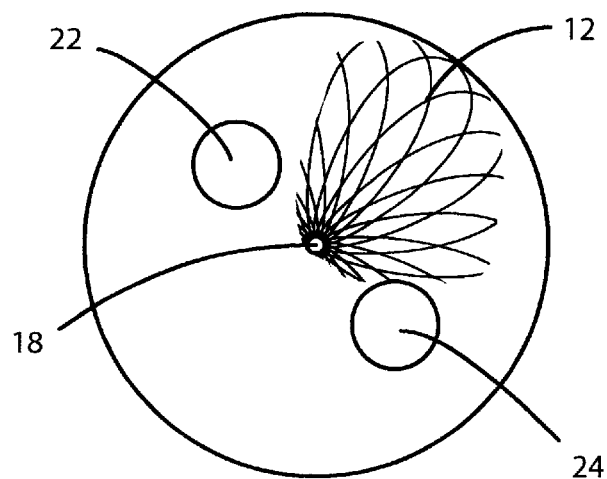
FIG. 2 is a front plan view of the device of FIG. 1.

As is illustrated in FIG. 1, the device, when in its unconstrained state, comprises a disk-like device 10 having opposed ends 12 and 14 of a predetermined expanded diameter and a hollow central portion 16 between the two ends. The metal fabric from whom the device 10 is formed comprises a plurality of wire strands that are woven or braided into a tubular configuration and then heat set in a mold in a manner described in U.S. Pat. No. 6,123,715 to Curtis Amplatz, the contents of which are hereby incorporated by reference.

As is described in the '715 patent, the wire strands comprising the metal fabric are preferably formed from a metal or metal alloy which is both resilient and which can be heat-treated to substantially set a desired shape into the woven fabric. Thus, the metal strands may be a cobalt-based, low thermal expansion alloy commonly referred to as Elgiloy, a nickel-based high temperature, high-strength "super alloy" commercially available from Haynes International under the trademark "Hastelloy", a nickel-based heat treatable alloy, such as Incoloy produced by International Nickel Company as well as a number of different grades of stainless steel. These materials all exhibit a suitable amount of deformation induced when placed in a mold and subjected to an elevated temperature for a prescribed period of time. So-called shape memory alloys such as Nitinol are especially well suited to the present application.

Figure 5:
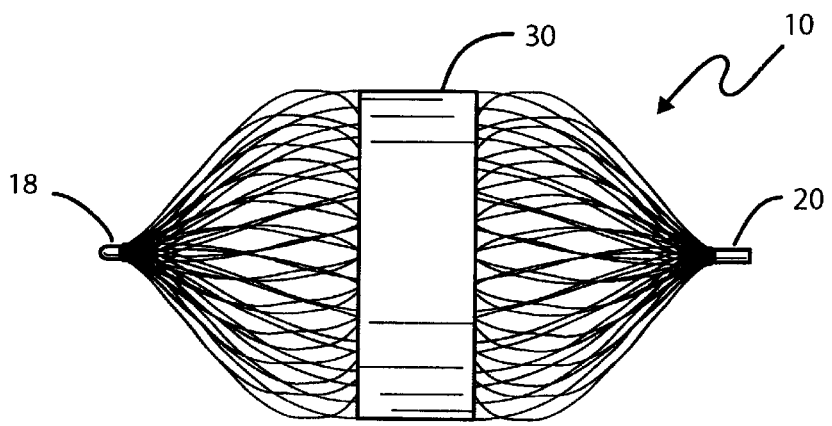
FIG. 5 is a side elevational view of the device of FIG. 1 in its deformed, lesser cross-sectional dimension state.

A tubular metal braid segment having a predetermined number of strands and a desired pick is cut from a longer piece thereof after clamp rings are crimped onto the tubular structure at predetermined spaced-apart locations prior to cutting the strands at the outer ends of the clamp rings. The crimped clamp rings are best seen in FIG. 5 and are identified by numerals 18 and 20, respectively and each may include an internally threaded bore, the purpose of which will be explained herein below.

Once an appropriately sized piece of the metal fabric is obtained, it is deformed to generally conform to a surface of a molding element. Placing the fabric within the mold functions reorient the relative position of the strands of the metal fabric from an initial order to a second, reoriented configuration. In the case of the present invention, the mold is generally cylindrical and of a predetermined length and diameter so that a braided device shaped within it is of a size allowing it to be placed within a tubular blood vessel, such as the pulmonary artery. After the braided device is placed in the mold, the mold and device are heated for a period of time sufficient to cause the tubular fabric, with its clamped ends, to take on the shape of the mold. The heat treatment depends primarily upon the metal or metal alloy employed for the wire strands and the time and temperatures are such that the device takes on the shape of the mold.

Those desiring additional information on the method for fabricating the flow restriction device of the present invention are again referred to the Amplatz '715 patent.

In forming the device 10, one or more cylindrical rods (not shown) are fitted through the braided fabric before the assembly is placed in the mold. When the cylindrical rods are later removed following the heat treatment step, the device is left with apertures, as at 22 and 24, formed through the end 12 of the device and apertures, as at 26 and 28, are formed through the second end 14. The aperture 22 is longitudinally aligned with the aperture 26 and the aperture 24 is longitudinally aligned with the aperture 28. While the device illustrated in FIGS. 1–4 is shown as having two lumens through the thickness dimension of the device, a greater or fewer number may be formed so long as the effective cross-sectional area of the apertures provides a desired pressure drop there across.

To inhibit fluid flow through the restrictor device 10 except by way of the lumens, it may prove expedient to include a non-metallic fibrous material, such as-a polyester fabric, in the space between the two ends, being careful so that the fabric does not invade the openings defined by the apertures 22–28. It has also been found expedient to wrap a PTFE fabric band 30 around the periphery of the device to inhibit tissue ingrowth. The use of band 30 makes it easier to retrieve the restrictor device 10 prior to the surgical repair of the defects.

Figure 6:
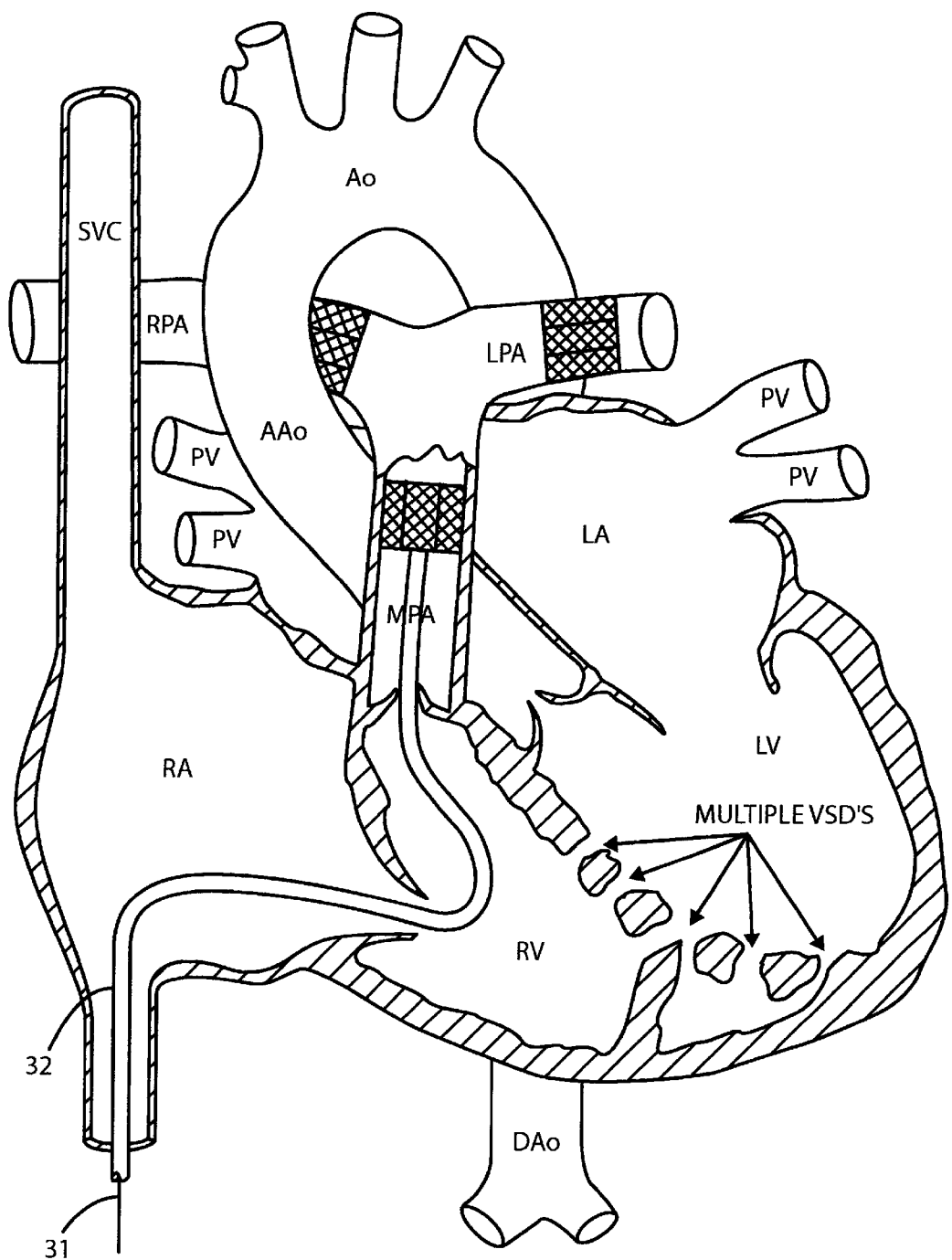
FIG. 6 is an anatomical drawing of the device of FIG. 1 installed as a flow restrictor in the main pulmonary artery of a heart.

In treating patients requiring pulmonary banding, the device 10 is first affixed to a threaded distal end of a pusher device, such as a cable or an elongated guidewire 31, to a threaded bore on one of the clamps 18 or 20 and then drawn into a tubular loading member used to load the device 10 into the proximal end of a guiding catheter by stretching the device longitudinally to thereby greatly reduce its external diameter. Once the device, and the pusher device 31 affixed to it, are contained within the lumen of the guide catheter which is indicated generally by numeral 32 in FIG. 6, the guide catheter is routed through the vascular system into the right atrium (RA) and then through the tricuspid valve into the right ventricle (RV) and, then, the main pulmonary artery (MPA) or alternatively in the right pulmonary artery (RPA) or the left pulmonary artery (LPA). With the distal end of the guide catheter in one of the MPA, the RPA and the LPA pusher device 31 is used to push the device 10 out from the confines of the distal end of the guiding catheter 32, where-upon the device 10 springs back to its normal unconstrained state where it becomes lodged crosswise in the selected pulmonary artery to thereby restrict blood flow from the right ventricle into the lungs. Blood flow is only permitted through the openings 22, 24 and 26, 28 formed through the thickness dimension of the device 10. By appropriately sizing the openings, blood pressure in the right pulmonary artery (RPA) and the left pulmonary artery (LPA) can be maintained at a level that will not result in symptoms of congestive heart failure.

The device may be left in place for a sufficient period of time for an infant to reach a point where surgery to correct the septal defects can be better tolerated. At this time, the device 10 can be removed by catheter technique or surgery. The fabric band 30 covering the periphery of the device helps reduce tissue ingrowth, making it easier to withdraw the device 10 at the time that the septal defect(s) are repaired.

Without limitation, the tubular braid used in constructing the device 10 may have a relaxed diameter of about 30 mm with a pitch of about 50° and a pick of about 72. With such a construction, it may be advisable to include a fibrous mass within the confines of the device 10 to improve its occluding properties. We have found, however, that by increasing the braid pick to include up to 144 per linear inch, the need to include such a fibrous mass is eliminated. The braid itself is sufficiently dense to obstruct blood flow except through the preformed openings that extend through the thickness dimension of the device.

Figure 3:
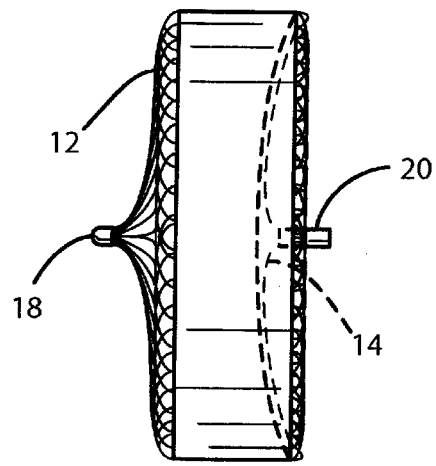
FIG. 3 is a side elevational view of the device of FIG. 1.
Figure 4:
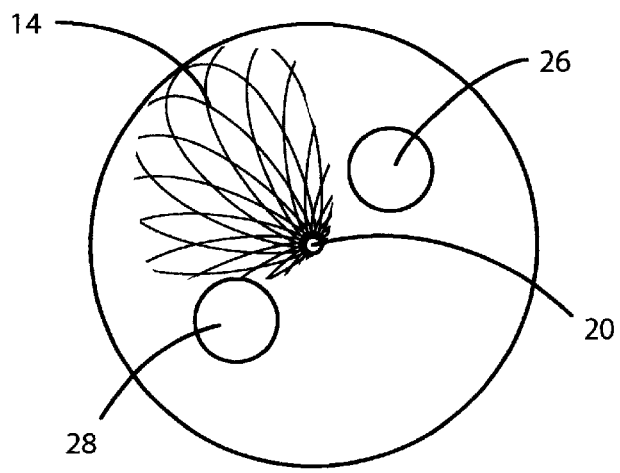
FIG. 4 is a rear elevation of the device of FIG. 1.

While the device 10 is preferably molded so as to have the configuration of a thin disk or a right circular cylinder, it has also been found desirable in some applications to have one of the end surfaces slightly convex and the opposite end surface slightly concave as is indicated in the side elevational view of FIG. 3.

While the device of the present invention to this point has been described in connection with its use in controlling blood pressure in the pulmonary arteries for addressing pulmonary vascular disease to establish its utility, it may also be used in carrying out other medical procedures. Newborns having a heart defect know as Transposition of the Great Arteries (TGA) may undergo the Rashkind procedure referred to as a "balloon septostomy" or a variation thereof called a "blade septostomy". In a balloon septostomy a catheter with an uninflated balloon at its distal end is inserted into the vascular system and advanced into the heart. The balloon catheter is made to pass through an opening in the atrial septum called the "foramen ovale" into the left atrium. The balloon is then inflated and withdrawn, tearing the atrial septum as it is pulled back into the right atrium. The enlarged opening allows an increase of oxygenated blood flowing to the aorta and then to the body.

The device of the present invention can be employed to more precisely control the blood flow through the tear in the atrial septum. By selecting a flow restricting device with appropriately sized lumens therethrough, more precise control of oxygenated blood flow to the aorta can be realized. The device 10 can be inserted into the balloon-enlarged opening in a manner similar to the procedure previously described for placing the device in a pulmonary artery.

The device 10 may also find application in treating patients with portal hypertension because of transhepatic portosystemic shunts. This condition may lead to ectopic varices and gastrointestinal bleeding. By decreasing the blood pressure in the high pressure portal system, controlled level of occlusion of the large hepatic vein can be accomplished. The procedure involves passing a catheter through the right internal jugular vein into the right hepatic vein. A needle is then passed anteriorly into the portal vein. The tract is dilated and the device 10 may be inserted and used to maintain patency.

Yet another surgical procedure where the present invention finds application is in the fenestrated Fontan operation. One congenital heart abnormally leaves an infant with only a single functional ventricle. The right ventricle for delivering blood to the lungs may be non-functional. Dr. Francois Fontan came up with a surgical solution in which the vena cava carrying blood returning from the body is connected directly to the pulmonary arteries and thereby oxygenated. Many patients so treated, however, develop a condition called protein-losing enteropathy. Symptoms of this ailment include abdominal, shin and ankle swelling, diarrhea and abdominal discomfort. Where drug treatment fails, a more aggressive approach involves surgery to create a fenestration in the Fontan channel that allows shunting across from the right to the left side of the heart.

The present invention permits a minimally invasive catheterization procedure to create the fenestration and to then install an appropriately sized flow restrictor in the fenestration to better control the volume rate of flow through the fenestration by preventing occlusion, improving the patient's symptoms and thereby the degree of cyanosis.

This invention has been described herein in considerable detail in order to comply with the patent statutes and to provide those skilled in the art with the information needed to apply the novel principles and to construct and use such specialized components as are required. However, it is to be understood that the invention can be carried out by specifically different equipment and devices, and that various modifications, both as to the equipment and operating procedures, can be accomplished without departing from the scope of the invention itself.

What is claimed is:

1. A collapsible medical device, comprising a plurality of metal strands woven into a woven metal fabric having a proximal end and a distal end, each end having a means for securing each end attached to said woven metal fabric, thereby gathering said strands and inhibiting unraveling of the strands, said woven metal fabric having an expanded preset configuration shaped to create a restriction in a blood vessel, said expanded preset configuration being in a shape of a cylindrical disk of a predetermined thickness having at least one enlarged lumen extending through the thickness dimension of said disk through which blood may flow and deformable to a lesser cross-sectional dimension for delivery through a channel in a patient's body, the woven metal fabric having a memory property whereby the medical device tends to return to said expanded preset configuration when unconstrained.

2. The medical device as recited in claim 1, wherein at least one of the said means for securing each end has a threaded bore adopted for rotational attachment to a delivery device.

3. The medical device as recited in claim 2, further including an occluding fiber material retained within a hollow central portion formed by said woven fabric.

4. The medical device as recited in claim 1, wherein the metal fabric is manufactured from an alloy selected from the group consisting of stainless steel, nickel-titanium, and cobalt-chromium-nickel.

5. The medical device as recited in claim 4, further including an occluding fiber material retained within a hollow central portion formed by said woven fabric.

6. The medical device as recited in claim 1, further including an occluding fiber retained within a hollow central portion formed by said woven fabric.

7. A collapsible medical device, comprising: a tubular woven metal fabric including a plurality of braided strands and having a first end and a second end, each end having a clamp attached to said metal fabric to thereby gather said strands together and inhibit unraveling of the stands, said metal fabric having a collapsed configuration for delivery through a channel in a patient's body and a generally cylindrical disk-shaped expanded preset configuration, with an enlarge aperture formed through a thickness dimension thereof for substantially creating a restriction without totally occluding blood flow in a body organ.

8. The medical device as recited in claim 7 wherein one of said two opposed ends is concave.

9. The medical device as recited in claim 7 wherein a volume disposed between the first and second ends contains a non-metallic fibrous material.

10. The medical device as recited in claim 9 wherein each of the first and second ends includes said aperture, the apertures in the first and second ends being longitudinally aligned and not occluded by the fibrous material.

11. The medical device as recited in claim 10 and further including a band of non-metallic fibrous material covering a periphery of the cylindrical disk-shaped device.

12. The medical device of claim 11 wherein the band comprises PTFE.

13. A collapsible medical device, comprising a woven metal fabric including a plurality of braided strands and having a proximal end and a distal end, each end having a clamp attached to said tubular woven metal fabric to thereby gather said strands together and inhibit the strands from unraveling, said woven metal fabric having an expanded preset configuration shaped to create a restriction to blood flow in a body organ, said expanded preset configuration being disk-shaped and deformable to a lesser cross-sectional dimension for delivery through a channel in a patient's body, wherein the expanded preset configuration comprises two expanded diameter end portions and a hollow central portion, said expanded diameter portions having a diameter to span a patient's pulmonary artery, the end portions and the central portion including enlarged openings of a predetermined size substantially less than the size of the expanded diameter portions therein through which blood may flow, the woven metal fabric having a memory property whereby the medical device tends to return to said expanded present configuration when unconstrained.

14. The medical device as recited in claim 13, wherein one of said clamps has a threaded bore adapted for rotationally receiving a delivery device.

15. The medical device as recited in claim 13, further including an occluding fiber contained within said hollow center portion.

16. The medical device as recited in claim 13, wherein the metal fabric is manufactured from an alloy selected from the group consisting of stainless steel, nickel-titanium, and cobalt-chromium-nickel.

17. The medical device as in claim 13 and further including a band of non-metallic fabric material covering a periphery of the central portion.

18. The medical device as in claim 17 wherein the band comprises PTFE.

* * * * *

UNITED STATES PATENT AND TRADEMARK OFFICE
Certificate

Patent No. 6,638,257 B2                                                                                          Patented: October 28, 2003

On petition requesting issuance of a certificate for correction of inventorship pursuant to 35 U.S.C. 256, it has been found that the above identified patent, through error and without any deceptive intent, improperly sets forth the inventorship.
Accordingly, it is hereby certified that the correct inventorship of this patent is: Kurt Amplatz, St. Paul, MN (US); and Mark M. Boucek, Golden, CO (US).

Signed and Sealed this Seventh Day of August 2007.

MICHEAL J. HAYES
*Supervisory Patent Examiner*
Art Unit 3734

UNITED STATES PATENT AND TRADEMARK OFFICE
Certificate

Patent No. 6,638,257 B2                                      Patented: October 28, 2003

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Kurt Amplatz, St. Paul, MN (US); and Mark M. Boucek, Golden, CO (US).

Signed and Sealed this Fourth Day of September 2007.

MICHAEL J. HAYES
*Supervisory Patent Examiner*
Art Unit 3734